(12) United States Patent
Scholl et al.

(10) Patent No.: US 7,189,232 B2
(45) Date of Patent: Mar. 13, 2007

(54) DEVICES AND METHODS FOR CONTROLLING MOVEMENT OF AN ELECTROSURGICAL ELECTRODE

(75) Inventors: John A. Scholl, Danville, CA (US); Duane W. Marion, Santa Clara, CA (US); George A. Morrison, Redwood City, CA (US); Jeffrey A. Smith, Petaluma, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/433,272

(22) Filed: May 11, 2006

(65) Prior Publication Data

US 2006/0206106 A1    Sep. 14, 2006

Related U.S. Application Data

(63) Continuation of application No. 11/003,267, filed on Dec. 2, 2004, which is a continuation-in-part of application No. 10/714,126, filed on Nov. 13, 2003, now Pat. No. 7,060,063.

(60) Provisional application No. 60/426,030, filed on Nov. 13, 2002.

(51) Int. Cl.
*A61B 18/18* (2006.01)

(52) U.S. Cl. .......................................... 606/47; 606/45

(58) Field of Classification Search ................ 606/45, 606/47, 167, 170, 180
See application file for complete search history.

(56) References Cited

U.S. PATENT DOCUMENTS

| 5,417,687 | A   |   | 5/1995  | Nardella |           |
|-----------|-----|---|---------|----------|-----------|
| 5,437,664 | A   |   | 8/1995  | Cohen    |           |
| 5,472,441 | A   |   | 12/1995 | Edwards  |           |
| 5,507,743 | A   |   | 4/1996  | Edwards  |           |
| 5,794,626 | A   | * | 8/1998  | Kieturakis | .......... 600/567 |
| 5,928,159 | A   |   | 7/1999  | Eggers   |           |
| 5,947,964 | A   |   | 9/1999  | Eggers   |           |
| 5,976,128 | A   |   | 11/1999 | Schilling |           |
| 6,022,347 | A   |   | 2/2000  | Lindenmeier |         |
| 6,022,362 | A   | * | 2/2000  | Lee et al. | .......... 606/159 |
| 6,080,149 | A   |   | 6/2000  | Huang    |           |
| 6,102,908 | A   | * | 8/2000  | Tu et al. | .......... 606/41 |
| 6,106,524 | A   |   | 8/2000  | Eggers   |           |
| 6,277,083 | B1  |   | 8/2001  | Eggers   |           |
| 6,287,304 | B1  | * | 9/2001  | Eggers et al. | ...... 606/37 |
| 6,312,428 | B1  |   | 11/2001 | Eggers   |           |
| 6,331,166 | B1  | * | 12/2001 | Burbank et al. | ..... 600/567 |
| D457,628  | S   |   | 5/2002  | Eggers   |           |
| D457,960  | S   |   | 5/2002  | Eggers   |           |
| 6,432,103 | B1  |   | 8/2002  | Ellsberry |           |
| 6,440,147 | B1  | * | 8/2002  | Lee et al. | .......... 606/159 |
| 6,471,659 | B2  |   | 10/2002 | Eggers   |           |
| 6,497,704 | B2  | * | 12/2002 | Ein-Gal  | .......... 606/41 |

(Continued)

*Primary Examiner*—Michael Peffley
*Assistant Examiner*—Alex Toy

(57) ABSTRACT

An electrosurgical electrode assembly having a cutting device including a catheter with a proximal and distal end, and an electrode carried on the distal end of the catheter. A controller is connected to the cutting device. A data acquisition system is connected to the controller and is capable of monitoring voltage and current output. A microprocessor may also be connected to the data acquisition system for processing voltage and current data from the data acquisition system. A generator is also connected to the data acquisition system. The controller initiates movement of the electrode upon arc initiation at the electrode. Methods of using the devices herein are also disclosed.

20 Claims, 6 Drawing Sheets

U.S. PATENT DOCUMENTS 6,620,157 B1    9/2003   Dabney
6,676,658 B2 *  1/2004   Burbank et al. .............. 606/45
6,770,070 B1    8/2004   Balbierz 2002/0072745 A1 *  6/2002   Truckai et al. ................ 606/47
2003/0073993 A1    4/2003   Ciarocca
2003/0120270 A1    6/2003   Acker

* cited by examiner

DEVICES AND METHODS FOR CONTROLLING MOVEMENT OF AN ELECTROSURGICAL ELECTRODE

This application is a continuation of U.S. application Ser. No. 11/003,267, filed Dec. 2, 2004, which is a continuation-in-part of U.S. application Ser. No. 10/714,126, filed Nov. 13, 2003 and now U.S. Pat. No. 7,060,063, which claims priority to U.S. Provisional Application Ser. No. 60/426,030, filed Nov. 13, 2002. This invention relates to devices and methods that may, but do not necessarily, involve the use of a target tissue localization device, such as shown in U.S. application Ser. No. 09/677,952, filed Oct. 2, 2000, now issued as U.S. Pat. No. 6,325,816, in conjunction with an electrosurgical loop-type cutter, such as shown in U.S. application Ser. No. 09/844,661, filed Apr. 27, 2001; U.S. application Ser. No. 09/588,278, filed Jun. 5, 2000, now issued as U.S. Pat. No. 6,530,923; and U.S. application Ser. No. 10/045,657, filed Nov. 7, 2001. All of the above-mentioned patents and applications are herein expressly incorporated by reference in their entirety.

FIELD OF THE INVENTION

The present invention relates generally to an electrosurgical electrode system that is capable of excising a tissue sample using a system enhanced by impedance feedback during the movement of the cutting element.

BACKGROUND

Typical electrosurgical procedures, such as cutting or cautery procedures, are performed with a hand held device, which the user can manipulate as the RF energy is delivered in order to facilitate the creation of the desired effect at the electrode. The ability to visually see the electrode and to change the proportion of the electrode that is held in contact with the tissue allows the user to adjust the motion or position of the device with respect to the activity observed at the electrode to compensate for the constant power output of a commercial electrosurgical generator and to force the generator to achieve the desired effect. With a percutaneous procedure, in particular an automated, percutaneous procedure, this type of user-based control is not possible, since the electrode is, in many cases, not visible. And in the case of automated control, the effects occur too quickly to allow human reaction. In this case, it is advantageous to have an automated method to evaluate the effect at the electrode and a method to determine when specific events have occurred and initiate the appropriate action. Of specific concern in a procedure requiring the cutting or excision of tissue is the creation of an arc at the electrode, since an arc permits the vaporization of tissue, which is the phenomenon that creates the cut.

For manual systems, where the cutting loop is deployed and rotated by hand by the user, other problems exist. The user may not know if the electrode movement is too slow, which leads to too much RF energy exposure that can result in excessive thermal damage and/or vaporization of the intended tissue sample. If, on the other hand, the electrode movement is too fast, this could result in a weak cutting arc or total loss of the cutting arc, which could result in undersized or mechanically damaged specimens.

This invention utilizes the measurements of the electrical characteristics of the tissue and correlates them to a physical effect at the electrode, which is then used to signal the user to make appropriate adjustments in the method.

SUMMARY OF THE INVENTION

The present invention relates to devices and methods for using an electrosurgical electrode to excise a tissue sample from a patient. More particularly, the invention provides a system that includes a means for monitoring the appropriate time to initiate movement of the cutting device.

In one embodiment, the electrosurgical electrode assembly includes a cutting device having a catheter with a proximal and distal end. The cutting device also has an electrode carried by the distal end of the catheter. The proximal end of the cutting device is a handpiece that may be reusable or disposable, or a combination thereof. In particular, the handle of the handpiece may be reusable and the electrode inserted into the handle may be disposable. A controller is connected to the cutting device. A data acquisition system is connected to the controller that is capable of monitoring voltage and current output. The system also contains a microprocessor connected to the data acquisition system, which is capable of processing voltage and current data from the data acquisition system. An electrosurgical generator is also connected to the data acquisition system. In operation, the controller initiates movement of the electrode upon arc initiation at the electrode.

In another embodiment, the system also includes an electrically isolated switch connecting the data acquisition system and the controller. The electrically isolated switch may be an optical switch.

In another embodiment, the controller, data acquisition system, electrosurgical generator, and microprocessor are integrated into a single control unit. The control unit may be able to drive DC motors that are located in the reusable handpiece of the cutting device.

In another embodiment, the electrosurgical electrode assembly includes a cutting device having a catheter with a proximal and distal end. The cutting device also has an electrode carried by the distal end of the catheter. The proximal end of the cutting device is a handpiece that may be reusable or disposable, or a combination thereof. In particular, the handle of the handpiece may be reusable and the electrode inserted into the handle may be disposable. A controller is connected to the cutting device. A data acquisition system is connected to the controller that is capable of monitoring voltage and current output. The data acquisition system is providing feedback information to the controller through the arc detection cable. An electrosurgical generator is also connected to the data acquisition system. The output from the electrosurgical generator passes through the data acquisition system and the controller to the patient through the handpiece. In operation, the controller switches on the electrosurgical energy to the electrode and initiates movement of the electrode upon arc initiation at the electrode based on feedback information from the arc detection cable. In an alternative embodiment, the system may also include a microprocessor connected to the data acquisition system. The microprocessor may include logic to calculate the load (or electrical) impedance so that it may determine the presence of an arc.

In yet another embodiment, the electrosurgical electrode assembly includes a cutting device having a catheter with a proximal and distal end. The cutting device also has an electrode carried by the distal end of the catheter. The proximal end of the cutting device is a handpiece that may be reusable or disposable, or a combination thereof. In particular, the handle of the handpiece may be reusable and the electrode inserted into the handle may be disposable. The assembly also includes a control unit connected to the cutting device. This integrated control unit contains an electrosurgical generator connected to the cutting device and a data acquisition system connected to the generator that is capable of monitoring voltage and current output. The control unit also contains a microprocessor connected to the data acquisition system, which is capable of processing voltage and current data from the data acquisition system, and a controller connected to the data acquisition system. In operation, the controller initiates movement of the electrode upon arc initiation at the electrode.

In another embodiment, the microprocessor of the systems described above includes logic to calculate the load (or electrical) impedance from the current and voltage output. By monitoring the change in the load (electrical) impedance value, the presence of an arc can be determined. The presence of the arc could also be determined by monitoring any one, or a combination, of the following electrical characteristics: electrical impedance, a change in electrical impedance, voltage, a change in voltage, current, or a change in current.

In another embodiment, the systems include a return electrode connected to the electrosurgical generator.

In yet another embodiment, the electrode has a proximal part and a distal part. The distal part of the electrode is movable between a retracted state and an outwardly extending operational state. A first driver may also be operably coupled to the electrode, where the first driver can move the electrode from the retracted state and/or rotate the electrode about its axis in order to separate a tissue section from the surrounding tissue by moving the electrode. In addition to rotating the electrode, the electrode may also be moved translationally or in any other way to effect separation of the tissue section from the surrounding tissue.

The methods of the present invention relate to controlling the initial movement of an electrosurgical electrode. Energy is delivered to an electrosurgical electrode. The electrical characteristics associated with the electrosurgical electrode are then monitored. This monitoring step may include monitoring any one, or a combination, of the following electrical characteristics: electrical impedance, a change in electrical impedance, voltage, a change in voltage, current, or a change in current. The initiation of an arc is then determined based on the monitoring step. The electrosurgical electrode is then moved once the arc has been detected. In one embodiment, the electrode may be moved automatically once the arc has been detected. The energy being delivered to the electrosurgical electrode may then be adjusted based upon the monitoring step in an effort to help maintain an effective arc. In addition, the speed of the electrosurgical electrode may also be adjusted based on the monitoring step in an effort to help maintain an effective arc.

The methods of the present invention also relate to controlling the operation of a percutaneously-placed electrosurgical electrode of an electrosurgical device. Energy is first delivered to a percutaneously-placed electrosurgical electrode to create an arc at that location, while the electrode is stationary. The electrical characteristics associated with the electrosurgical electrode are then monitored. The electrical characteristic being monitored may be any one, or a combination, of the following: electrical impedance, a change in electrical impedance, voltage, a change in voltage, current, or a change in current. Once the creation of a cutting arc is established between the adjacent tissue and the electrode, the controller initiates movement of the electrode to effect separation of the tissue section from the surrounding tissue. The energy being delivered to the electrosurgical electrode may then be adjusted based upon the monitoring step in an effort to help maintain an effective arc.

In another method of controlling the operation of a percutaneously-placed electrosurgical electrode of an electrosurgical device, the percutaneously-placed electrosurgical electrode may be moved along a predetermined path while energy is being delivered. An electrical characteristic associated with the electrode may be monitored at the electrode. The electrical characteristic being monitored may be any one, or a combination, of the following: electrical impedance, a change in electrical impedance, voltage, a change in voltage, current, or a change in current. An expected position of the electrode along the predetermined path may also be monitored. The energy delivered to the electrode may then be adjusted based on the monitoring steps of the electrical characteristic and expected position in order to maintain an effective arc. In one embodiment, the electrical characteristic being monitored is electrical impedance.

In another method for controlling the movement of an electrosurgical electrode of an electrosurgical device within a target tissue, the electrosurgical electrode may be inserted into the target tissue. Energy is delivered to the electrosurgical electrode, which is then moved to cut the target tissue. The electrosurgical electrode can be rotated, translated, or any combination thereof, in order to accomplish the cutting of the target tissue. The electrode may be moved either automatically or manually. In another embodiment, the electrode is moved manually. An electrical characteristic associated with the electrosurgical electrode is monitored while the electrode is moved. The speed of the electrosurgical electrode can be adjusted based on the monitoring step in order to maintain an effective arc. The electrical characteristic being monitored may be any one, or a combination, of the following: electrical impedance, a change in electrical impedance, voltage, a change in voltage, current, or a change in current. In a preferred embodiment, electrical impedance or a change in electrical impedance is monitored. The method may also include the step of providing feedback to a user based on the monitoring step, wherein the user can adjust the speed based on the feedback. Alternatively, in an integrated system, the speed may be automatically adjusted based on the feedback. The feedback can comprise audio feedback, visual feedback, or any combination. Furthermore, the energy delivered to the electrosurgical electrode may also be adjusted based on the monitoring step in order to maintain an effective arc. The electrical characteristic may also be monitored to determine when an arc has been initiated before moving the electrode.

In another method for controlling the movement of a percutaneously-placed electrosurgical electrode of an electrosurgical device within a target tissue, the electrosurgical electrode may be inserted into the target tissue. Energy is delivered to the electrosurgical electrode to create an arc thereat while moving the electrode to cut the target tissue. The electrosurgical electrode can be rotated, translated, or any combination thereof, in order to accomplish the cutting of the target tissue. The electrode may be moved either automatically or manually. In a preferred embodiment, the electrode is moved manually. An electrical characteristic associated with the electrosurgical electrode is monitored while the electrode is moved. The speed of the electrosurgical electrode can be adjusted based on the monitoring step in order to maintain an effective arc. The electrical characteristic being monitored may be any one, or a combination, of the following: electrical impedance, a change in electrical impedance, voltage, a change in voltage, current, or a change in current. In a preferred embodiment, electrical impedance or a change in electrical impedance is monitored. The method may also include the step of providing feedback to a user based on the monitoring step, wherein the user can adjust the speed based on the feedback. Alternatively, in an integrated system, the speed may be automatically adjusted based on the feedback. The feedback can comprises audio feedback, visual feedback, or any combination. Furthermore, the energy delivered to the electrosurgical electrode may also be adjusted based on the monitoring step in order to maintain an effective arc. The electrical characteristic may also be monitored to determine when an arc has been initiated before moving the electrode.

As discussed above, the devices of the present invention monitor an electrical characteristic of the electrosurgical electrode during initiation of the arc. The electrical characteristic being monitored may be any one, or a combination, of the following: electrical (or load) impedance, a change in electrical (or load) impedance, voltage, a change in voltage, current, or a change in current. In a preferred embodiment, the system monitors for an electrical impedance value over 500 ohms. In another preferred embodiment, the system monitors for an electrical impedance value over 2-times a baseline electrical impedance value. This electrical impedance value is measured at very low power, usually below the level that is known to create an arc at the electrode. In yet another preferred embodiment, the system monitors for an electrical impedance value of 2.5-times a baseline electrical impedance value.

As discussed above, in addition to monitoring an electrical characteristic during the initiation of the arc as described above, the devices of the present invention monitor an electrical characteristic of the electrosurgical electrode during the movement of the electrosurgical electrode. The electrical characteristic being monitored may be any one, or a combination, of the following: electrical (or load) impedance, a change in electrical (or load) impedance, voltage, a change in voltage, current, or a change in current. In a preferred embodiment, the system monitors impedance values to determine if the speed of the electrode should be varied. Low impedance values signal that the electrode should be moved slower to avoid losing a good cutting arc. Low impedance values can be in the range of about 700–1200 ohms, alternatively between about 600–1200 ohms, alternatively below about 800 ohms, alternatively below about 900 ohms, alternatively below about 1000 ohms. High impedance values are indicative of the establishment of a strong cutting arc. Impedance values above about 1200 ohms, alternatively above about 1300 ohms, alternatively above about 1500 ohms, alternatively above about 2000 ohms, indicate a strong cutting arc. In some instances, impedance values may be in the range of 2500–3000 ohms.

In another embodiment, a manually controlled system could be utilized according to the following steps:

(1) Align the electrode at the proper location in the tissue.
(2) Turn on the RF energy.
(3) Wait for the system to recognize that a cutting arc has been created.
(4) Start manual movement of the electrode.
(5) Move the device quickly through the tissue, while maintaining high impedance (e.g., above about 1200 ohms).
(6) Slow the rotation if the load impedance falls to a level where the arc is struggling (e.g., 700–1200 ohms).
(7) Stop the electrode movement if the load impedance falls below about 700 ohms.
(8) Resume electrode movement once the load impedance rises (e.g., above about 1200 ohms).

Indicator lights on the front panel of the device may indicate to the user when the speed the should be varied. For example, a green light may be used to signal to "go" (continue moving the electrode), where the impedance value is above, e.g., about 1200 ohms. A yellow light may be used to indicate "slow down," where the impedance value is between about 700–1200 ohms. A red light may be used to indicate "stop," where the impedance falls below about 700 ohms.

A still further aspect of the invention is directed to a method for creating a tissue section within surrounding tissue. The method includes positioning a distal end of the catheter assembly at a target location within a breast of a patient. An elongate tissue separator element, at the distal end of the catheter assembly, is moved to a radially extended, outwardly bowed, operational state. Energy is supplied to the separator element. The separator element is automatically rotated about the axis, following at least the start of the separator element moving step, so to separate a tissue section from surrounding tissue. A tissue holding element, located at the distal end of the catheter assembly, is moved from a retracted condition to an extended, tissue engaging condition. The separated tissue section is surrounded by a tubular braided element by moving the tubular braided element, located at the distal end of the catheter assembly, from a proximal, radially contracted state to a distal, radially expanded state following the automatically rotating step.

Figure 1:
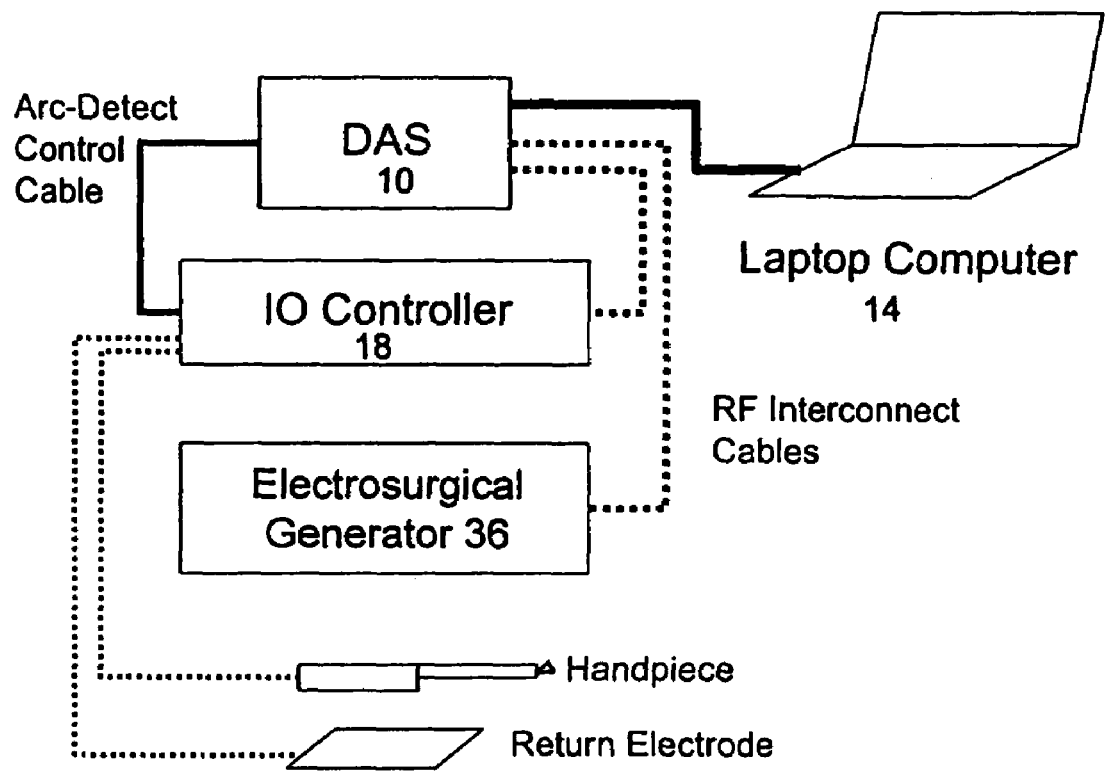
FIG. 1 depicts a system for using an electrosurgical electrode.

A still further aspect of the invention is directed to a method for creating a tissue section within surrounding tissue. The method includes positioning a distal end of the catheter assembly at a target location within a breast of a patient. An elongate tissue separator element, at the distal end of the catheter assembly, is moved to a radially extended, outwardly bowed, operational state. Energy is supplied to the separator element. The separator element is automatically rotated about the axis, following at least the start of the separator element moving step, so to separate a tissue section from surrounding tissue. A tissue holding element, located at the distal end of the catheter assembly, is moved from a retracted condition to an extended, tissue engaging condition. The separated tissue section is surrounded by a tubular braided element by moving the tubular braided element, located at the distal end of the catheter assembly, from a proximal, radially contracted state to a distal, radially expanded state following the automatically rotating step.

DETAILED DESCRIPTION

A first embodiment uses a commercially available RF generator along with an "IO" Control Box that controls the RF output to the electrode or loop-type cutter and contains a stepper motor drive to deploy and rotate the loop electrode. The RF activation, loop deployment and rotation are an automated sequence controlled by a stepper motor drive unit within the IO controller. One activation technique includes actuating the RF for approximately 400 milliseconds prior to the start of the deployment/rotation of the loop, in order to allow time for an arc to be established at the loop electrode. (There is an additional 100 millisecond delay induced by the loop deployment mechanism, for a total delay of 500 milliseconds.) This type of open loop operation causes two potential areas of inefficiency. First, the arc could be created early in the 500 millisecond period, causing excessive damage to the tissue while the electrode is arcing prior to the start of deployment/rotation. The second, more severe possibility is that the rotation sequence would be started prior to the creation of an arc, causing an incomplete cut or damage to the loop electrode, resulting in an inadequate tissue sample being obtained.

To provide more repeatable performance, the creation of a closed-loop system has been proposed. Review of the data collected from both clinical and bench testing has indicated that there is a significant difference in the load impedance when the electrode is arcing and when it is merely delivering RF energy to the tissue. This is probably the result of two different factors, the first being the desiccation of tissue surrounding the electrode (and removal of electrolytic solution) and the second being the creation of a gas-filled space around the electrode. By monitoring the load impedance during operation, a device could be constructed that detects when an arc has been created, and could initiate the deployment/rotation of the loop electrode.

As depicted in FIG. 1, the first embodiment makes use of the Artemis Data Acquisition System ("DAS") 10, Artemis Medical, Inc., Hayward, Calif., validated hardware that collects RF voltage and current data during the operation of the system. This data is fed to a data-acquisition card (National Instruments DAQ 516) in a microprocessor 14 (in a laptop computer), which then uses this voltage and current data to calculate the delivered power and load impedance. In addition to the analog inputs required to monitor voltage and current, this data-acquisition card contains digital output channels which could be used to signal the stepper motor driver that the movement, i.e., deployment and/or rotation sequence is to be initiated. FIG. 1 shows the electrical interconnection of the components used in the system.

Figure 2:
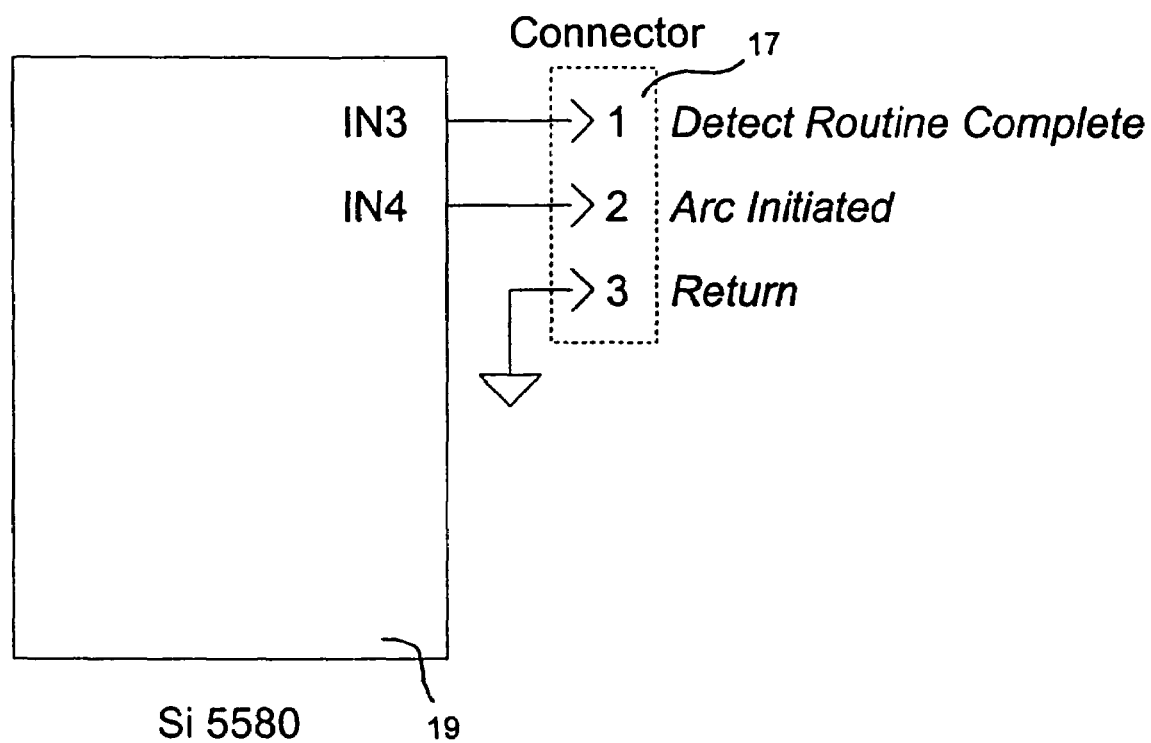
FIG. 2 depicts a diagram of the 10 controller of FIG. 1.

System Overview:

IO Controller 18: Additional signals need to be brought into the IO Controller 18, so that the motor deployment/rotation sequence can be initiated once an arc has been detected. There are an additional two unused inputs on the Si5580 Stepper Motor Driver 19 that have been wired to a unique connector 17 on the back panel of the controller 18. The circuit is shown in FIG. 2.

The operating software for the Si5580 drive unit 19 has been modified to check the status of these signals prior to starting the motor sequence. Once the arc detection routine has been completed, the "Detect Routine Complete" signal is transmitted from the laptop computer 14 through the DAS Data Acquisition System 10 and to the Si5580 drive unit 19. When this signal is received, and if the "Arc Initiated" signal is present, the deployment/rotation sequence is initiated. If an arc was not detected, the "Detect Routine Complete" signal is generated absent the "Arc Initiated" signal, instructing the Si5580 drive unit 19 to de-energize the RF output and abort the remainder of the sequence. In order to permit the operation of the IO Controller 18 without the DAS Data-Acquisition System 10, the Si5580 drive unit 19 checks if the "Detect Routine Complete" signal is absent initially, in which case the sequence is initiated using the 400 millisecond delay, without using any of the arc detection logic.

Figure 3:
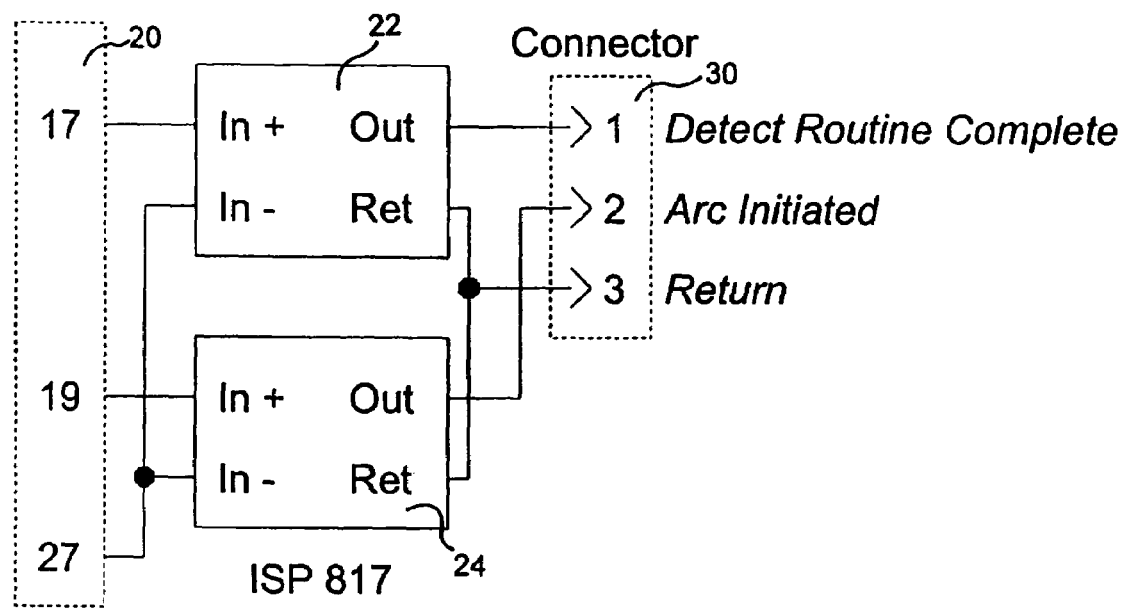
FIG. 3 depicts a diagram of the DAS data acquisition system of FIG. 1.

DAS Data-Acquisition System 10: As seen in FIG. 3, to electrically isolate the DAS System 10 from the IO Controller 18, the digital signals on the DAQ 516 card 20 were connected to two ISOCOM optically coupled isolators 22, 24, which provide 5.3 kVRMS of electrical isolation between the input and output. Optically coupled isolators 22, 24 are a means of transmitting a signal between two systems without having any direct electrical connection. In this system, the signals of the DAQ 516 cards 20 are connected to the inputs of the isolators and the outputs of the isolators are wired to a connector 30 on the enclosure, which is ultimately connected to the IO Controller 18 and the inputs to the Si5580 drive unit 19. When the digital signals on the DAQ card 20 are activated, a light emitting diode inside the isolator turns on, which then activates a phototransistor on the output of the isolator. This phototransistor provides the signal to the Si5580 drive unit 19, which allows light, rather than electrons, to become the transmission medium. This ensures that there is no possibility of any hazardous electric energy being transferred from one system to the other.

The Visual Basic program used for data-acquisition from the DAS Controller may be modified to check for an increase in impedance, which indicates that an arc has started. What is unique about this approach in the field of electrosurgery is the concept of monitoring the RF voltage and current output, thereby determining the load impedance (or other characteristic associated with the electrode) and using an observed change in that load impedance to start an automated procedure. It would also be possible to achieve a similar result by monitoring other electrical characteristics at the electrode, such as the delivered current or voltage, to determine when an arc has been initiated.

A review of the data files from bench and clinical testing indicated that typically the load impedance was below 400–450 ohms when the electrode had not initiated an arc. Once an arc was initiated, the load impedance increased to at least 700 ohms, and in most cases exceeded 1000 ohms. This information was taken into account to specify an initial value of, for example, 500 ohms as the threshold to determine when an arc has started. The software is preferably structured to allow the user (product designer) to alter this value to further refine the arc detection scheme.

A timeout routine may be incorporated into the software as a safety feature. If the arc impedance threshold is not attained within, for example, one second, indicating that an arc has not been created, the RF is de-energized, and the routine is aborted and the user is alerted of this fact.

There may be two digital signals used for the arc detection routine, "Detect Routine Complete" and "Arc Initiated". When the software determines that an arc has been established, it sets the "Arc Initiated" signal high, and then indicates that the detection routine has completed by initiating a high-to-low transition of the "Detect Routine Complete" signal. This logic is structured in such a way as to minimize the risk of a false positive signal being sent to the controller, since it is unlikely that a single failure would cause both the "Arc Initiated" signal to be set high and the "Detect Routine Complete" signal to be set low.

Figure 4:
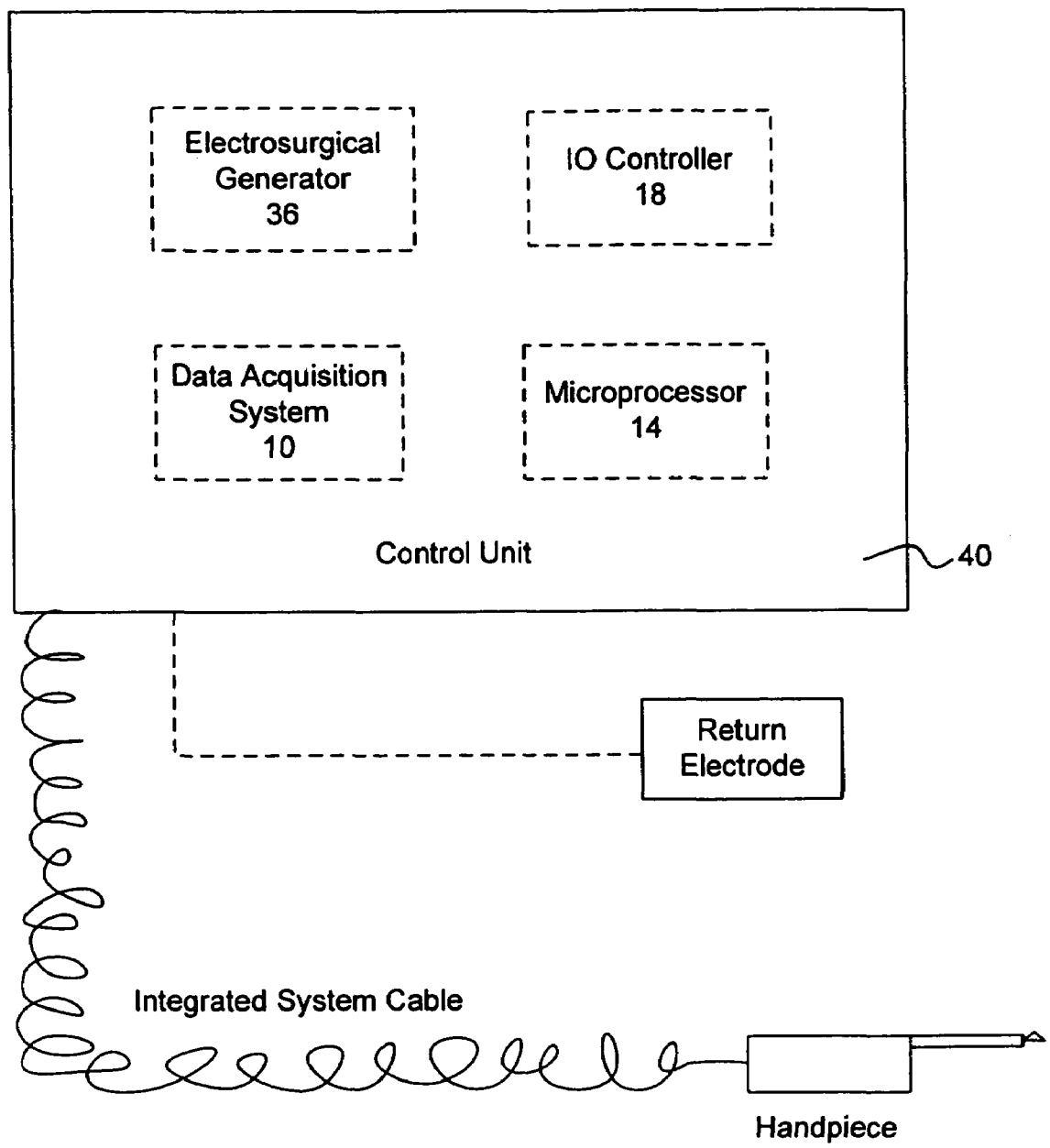
FIG. 4 depicts an integrated system for using an electrosurgical electrode with a fully integrated controller and generator.
Figure 5:
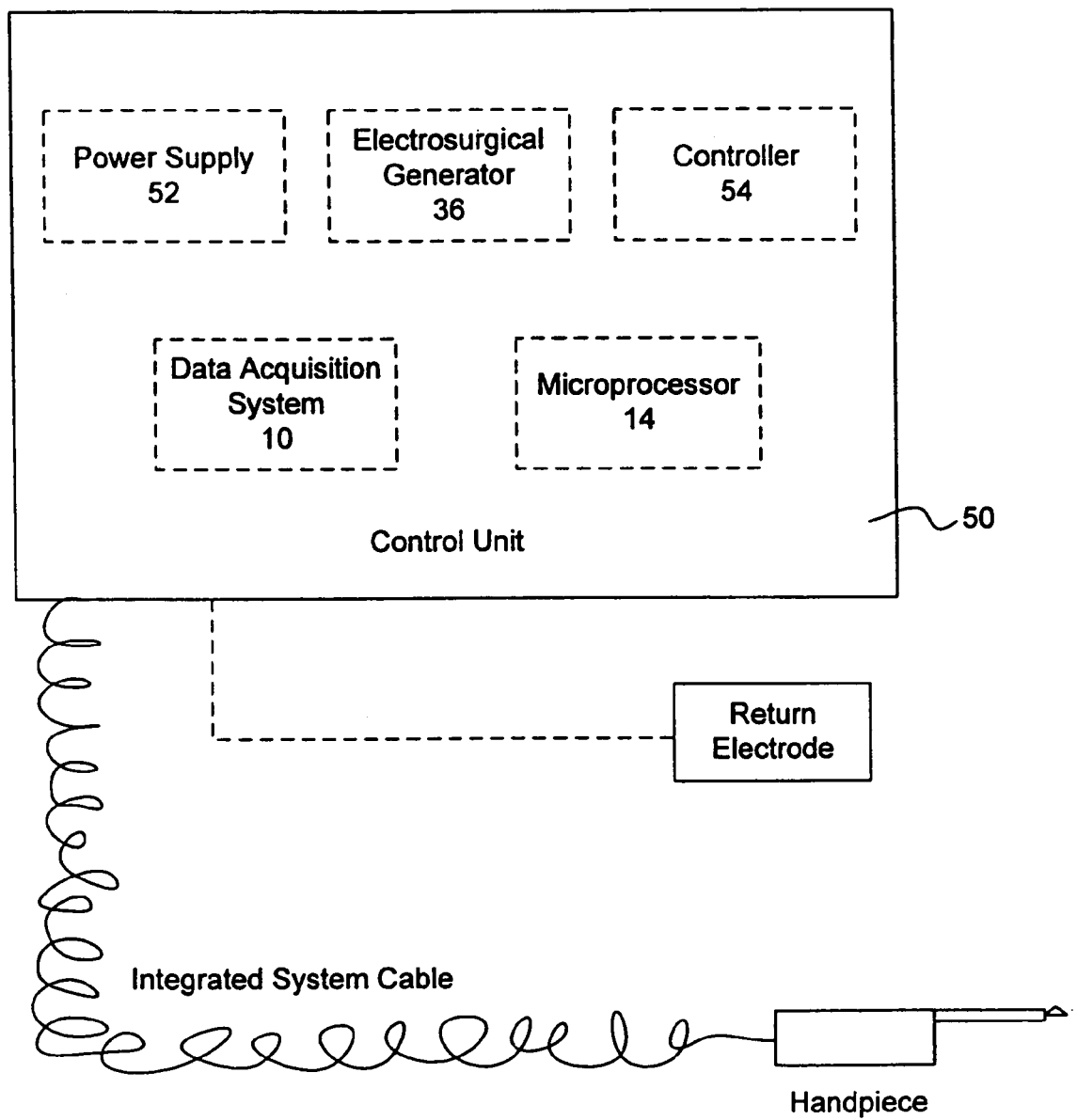
FIG. 5 depicts another integrated system for using an electrosurgical electrode with a fully integrated controller and generator.
Figure 6:
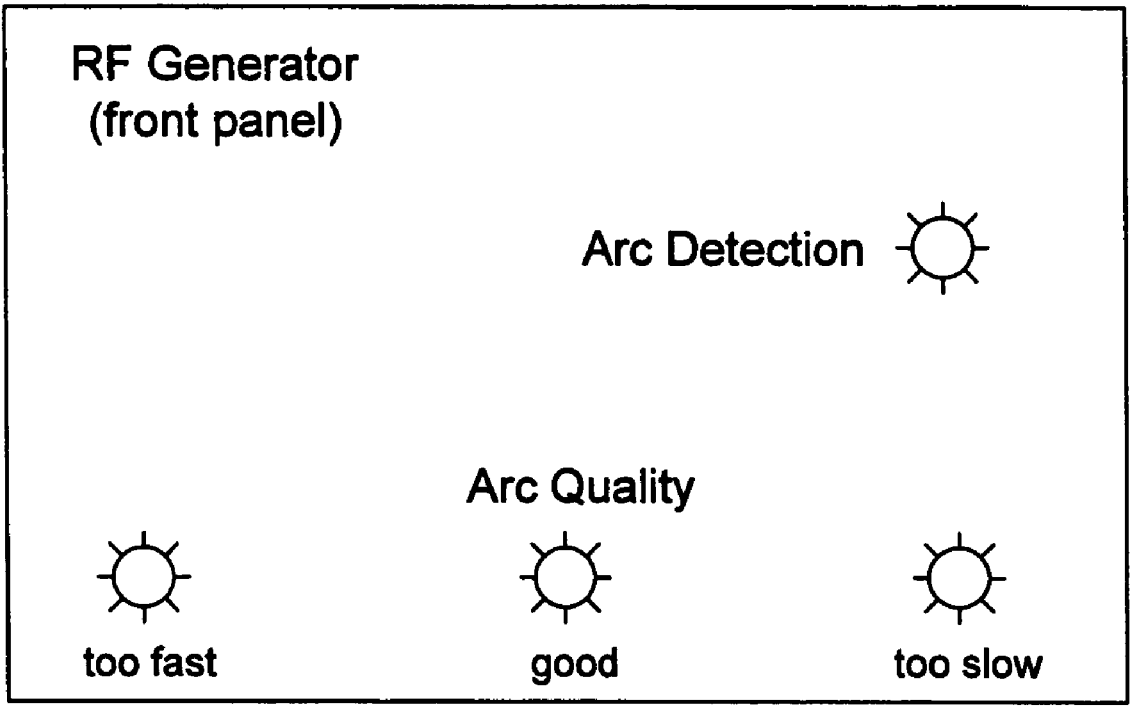
FIG. 6 depicts a front panel of an RF generator.

In another embodiment, as depicted in FIG. 4, the functionality of the RF (electrosurgical) generator 36, DAS 10, IO Controller 18, and microprocessor 14 is integrated into a single control unit 40. In yet another embodiment, the control unit 50 contains a power supply 52, RF (electrosurgical) generator 36, controller 54, DAS 10, and microprocessor 14 (see FIG. 6). These integrated systems allow the motor drive sequence and RF output to be controlled by a single microprocessor 14, which enhances the communication between the subsystems and allow additional signal processing. With this type of integrated system, it is possible to refine the control algorithms.

RF Output: With the other embodiment, the user sets the RF output power on the commercially available generator at the start of the procedure. There is no provision for an automated adjustment of this RF output power, since there is no communication between the microprocessor 14 (in the laptop computer) and the generator 36. With the integrated system of the preferred embodiment, however, it would be possible not just to signal the motor drive system to start movement or rotation in response to a change in load impedance, but it would also allow the RF output to be adjusted to compensate for changes in load condition. In contrast to other methods, which vary the speed of the cutting electrode through the tissue in response to changes in the load impedance, varying the RF output is advantageous since the system responds faster electrically than mechanically. With the preferred integrated system embodiment, the system monitors the performance during the automated sequence and makes adjustments during operation to reduce the incidence of failures. For example, if during the rotation sequence, the load impedance started to fall, the failure of the arc could be predicted, and the RF output increased in an effort to mitigate this failure. It would also allow the potential for adjusting the RF output with respect to the position of the cut wire, as it is likely that the RF output requirement is different at different points in the wire deployment/rotation sequence. As the cut process continues and as the sample is physically detached from the bulk tissue, the electrical characteristics may change, and the performance of the system could possibly be enhanced by making adjustments to the output during rotation to compensate for these changes. This could also be employed to use a higher output power to establish an arc, then cause the system to switch to a voltage control mode, where the output voltage rather than power is regulated, once the wire deployment process is started. This type of control provides an advantage, since a fixed output voltage causes the delivered power to increase in response to a lower load impedance, and to decrease in response to a higher load impedance. In this fashion, when the arc is created, and the impedance increases, the power is automatically reduced to mitigate thermal damage.

The RF algorithm control includes the following steps:
1. Find baseline impedance—deliver low power (approximately 5 W) for approximately 0.2–0.5 seconds and monitor load impedance, this sets a baseline value of impedance.
2. Initiate Arc—under power control, deliver high power output until an arc is detected by observing the load impedance increase approximately 2 to 3 times above baseline, preferably approximately 2 times above baseline. The high power output can be in the range of approximately 100–200 W. In a preferred embodiment, the high power output is approximately 170 W.
3. Dwell approximately 25–150 ms, preferably approximately 40 ms, allowing for the arc to stabilize.
4. Deploy cut wire—switch to fixed output voltage and extend electrode. The fixed output may be in the range of approximately 200–350 V. In a preferred embodiment, the fixed voltage output should range from approximately 240–260 V.
5. Dwell approximately 0–150 ms, preferably approximately 20 ms, maintaining voltage control and allowing the arc to stabilize.
6. Start electrode rotation—deliver fixed output cut voltage. This may be in the range of approximately 150–300 V, preferably 240–260 V.
7. Monitor impedance and recover arc if needed—monitor impedance and when it falls below approximately 2× the baseline value used in step 2, output approximately 170 W to re-initiate the arc. Alternatively, the output voltage could be increased to a higher, secondary level.

Motor Control: Using a single processor to control the RF output and the motor drive system also allows the motor speed to be regulated in response to changes in the load impedance. Different anatomical structures are comprised of different types of tissue, each of which has different electrical and physical properties. In general, there is a relationship between the density of the tissue and its electrical impedance. Dense, fibrous tissue typically has a lower level of hydration, which reduces its conductivity and increases its impedance. If this is taken into account, the arc detection system could also be used to regulate the speed of the motor drive system so that it is optimized for the specific tissue encountered. For example, once an arc is created, it would be possible on dense tissues for the cutting process to be further enhanced by slowing the speed of the electrode. On spongy or fatty tissues, which are relatively easy to cut, the thermal damage to the surrounding areas could be reduced by increasing the speed of the electrode, thereby minimizing the RF exposure. Furthermore, by monitoring the status of the tissue electrical properties, the system could allow a dwell time at specific points in the sequence, which could allow the arc to become more established and provide an improved cutting effect once motion is resumed. It could also determine if the arc at the electrode dissipated, at which point the motor could be stopped and the arc initiation and detection routine repeated.

User Control

Handpiece: The reusable handpiece has two buttons on it for user control of the system. One button is a "select" button that allows the user to toggle from one step of the procedure to the next. The other button is an "activate" button that allows the user to activate that step. For user convenience, the system also has an optional footswitch with two buttons that function as "select" and "activate" under the same manner as the handpiece switches.

In operation, in one embodiment, the user may perform the following steps:

Home the reusable handpiece—This step moves the motors and the mechanisms to a first position ready to receive the disposable insert. In particular, this step activates motor control to move the cut wire mechanism (CWM) and the Python/hook wire mechanism (PHWM) to a position ready to receive the disposable electrode insert.

Insert the disposable electrode—The user inserts the disposable electrode into the reusable handpiece and secures it with a ¼ turn rotation. The disposable electrode has an ID resistor in it that the reusable handpiece detects and communicates to the control box. If the resistance value is within a certain range, the system automatically programs itself for the proper disposable. The resistance value for a 15 mm cut disposable electrode is different that the resistance value for a 25 mm cut disposable electrode.

Ready for insertion—The disposable electrode comes with the capture Python and hook wire fully deployed. These are retracted into the shaft of the disposable electrode for device insertion into the patient.

Insertion—The user will create a skin incision to get the tip of the device under the skin. From there, the user gently pushes the device toward the intended target, e.g., a biopsy target. If tissue resistance is felt, the user can activate the RF electrodes at the tip of the instrument by tapping on the "activate" button. The details of the reusable handpiece, including the placement of the electrodes of the penetrating tip, are described in related U.S. application Ser. No. 10/374,582, filed on Feb. 25, 2003, entitled "Tissue Separating Catheter Assembly and Method," the entirety of which is hereby expressly incorporated by reference in its entirety.

Cut & capture sample—Once the device is in the proper position, the user activates the cut and capture sequence. Holding down the "activate" button for the duration of the cut activates the following steps: sending RF energy to the electrode, detecting the arc, moving the electrode, turning off the RF energy, stopping the electrode movement, and extending the hook wires and python. The user can also interrupt the cut sequence if desired.

Remove system from patient—The user withdraws the device with the cut sample from the patient.

Remove the sample from the device—The user hits the "activate" button to make the Python and hook wire retract from the sample. Once withdrawn, the user can use forceps to remove the cut sample from the device.

Remove the disposable from the reusable—The user releases a spring latch, counter-rotates the disposable electrode by ¼ turn, and removes the disposable electrode from the handpiece. The reusable handpiece can then be homed for insertion of another disposable electrode.

In a preferred embodiment, the integrated control box allows the user to start the cut sequence and stop it at any point. The user may elect to stop due to patient discomfort, or distraction in the room, etc. By releasing the "activate" button during the cut sequence, the RF energy is turned off and electrode movement stops. The system keeps track of the motor position to later re-activate and complete the movement. To restart the movement, the user again holds down the "activate" button and the system will repeat the startup RF algorithm above from the place it left off Percutaneous devices can benefit from using an RF activated penetrating electrode to ease placement. In yet another embodiment, RF energy is delivered to the distal tip of the device, creating a small arc to make an incision during penetration. Typically, the activation periods of such a device are very short, perhaps 500 to 1000 milliseconds. In this case, it is important to establish an arc as quickly as possible, but to minimize the power delivery in order to prevent damage to surrounding tissues. The same arc detection scheme could be employed to determine when an arc has been created, and then to limit the maximum power or voltage delivered to the tissue. It could also be used to reduce the time required to initiate an arc at the electrode, by delivering a higher initial output power, which would then be reduced once the arc was detected.

In another embodiment, a manually controlled system is used in which control of the electrosurgical electrode may be enhanced by monitoring and communicating feedback of a particular electrical characteristic to the user during operation. Energy is first delivered to an electrosurgical electrode to create an arc at that location, while the electrode is stationary. The electrical characteristics associated with the electrosurgical electrode are then monitored. The electrical characteristic being monitored may be any one, or a combination, of the following: electrical impedance, a change in electrical impedance, voltage, a change in voltage, current, or a change in current. With a manually controlled electrode, once the creation of a cutting arc is established between the adjacent tissue and the electrode, the user initiates movement of the electrode to effect separation of the tissue section from the surrounding tissue. The electrical characteristic can be continuously or periodically monitored and communicated to the user throughout the cutting process. The user can then adjust the speed at which the electrode is being moved through the tissue based on these electrical characteristics.

In one embodiment, the RF generator signals to the user whether the electrode movement should be faster to avoid excess tissue damage, or slower to avoid losing a good cutting arc. The user may receive electrical impedance feedback. An RF electrode will experience a shift from low impedance, for example, about 100–300 ohms, when in direct contact with the tissue, to high impedance, after a cutting arc has been established between the electrode and the tissue. Creation of a cutting arc involves the current jumping from the electrode through a small air gap into the tissue. The minimum impedance value that is indicative of the creation of a weak cutting arc is about 600–1200 ohms. The low arcing impedance values likely reflect arcing over a portion of the electrode and direct conduction to tissue contact to the electrode over a portion of the electrode. Total load impedance can be as high as about 2500–3000 ohms. Typically, the impedance values may be in the range of 1500–2500 ohms, alternatively 1200–2500 ohms, alternatively 1200–3000 ohms, alternatively 1500–3000 ohms.

After the cutting arc has been established, the RF generator for a manually operated system signals to the user that manual movement of the device should begin. During the excision, the RF generator signals the user when the speed of the electrode should be increased or decreased according to the electrical characteristic being monitored (e.g., electrical impedance level). The RF generator signal to the user could be audio or visual. For example, the RF generator could emit a series of sounds (e.g., beeps or chirps) that correspond to the level of the electrical characteristic. In one embodiment, the speed at which the sounds are emitted could increase or decrease in accordance with electrical characteristic (e.g., faster beeps may indicate a faster speed is needed). Alternatively, the pitch of the sound may vary accordingly (e.g., a higher pitch may indicate a faster speed is needed). In another embodiment, visual lights on the handpiece or the RF generator may signal to the user that an adjustment in speed is needed (e.g., different lights (see FIG. 6), different colored lights (not shown), or changing the frequency of blinking lights (not shown)). Alternatively, an analog or digital scale on the generator front panel or on an associated instrument may provide feedback to the user.

For minor fluctuations in the monitored impedance values, the system could be switched to a voltage control mode, where the output voltage rather than the power is regulated. As explained above, this type of control provides an advantage in that a fixed output voltage causes the delivered power to increase in response to a lower load impedance, and to decrease in response to a higher load impedance. Accordingly, when the arc is created, and the impedance increases, the power is automatically reduced to mitigate thermal damage. For larger fluctuations in the monitored impedance values, the user could use the feedback systems described above and alter the speed of the electrode accordingly.

In some instances, the cutting arc may be extinguished during the procedure. If this occurs, the electrical impedance would drop below about 500 ohms, or alternatively drops below about 2 times a baseline electrical value, or alternatively drops below about 2.5 times a baseline electrical value. If the cutting arc has been extinguished, the user should stop the rotation of the instrument, and then restart the method by turning the RF power back on and detecting when the arc has once again been established before resuming rotation.

Although the foregoing invention has, for purposes and clarity of understanding, been described in some detail by way of illustration and example, it will be obvious that certain changes and modifications may be practiced which will still fall within the scope of the appended claims.

We claim:

1. A method for controlling the movement of an electrosurgical electrode of an electrosurgical device within a target tissue comprising:
    inserting the electrosurgical electrode into the target tissue;
    moving the electrode to a radially extended, outwardly bowed, operational state;
    initiating the delivery of energy to an electrosurgical electrode to cut a target tissue;
    rotating the electrosurgical electrode;
    monitoring an electrical characteristic associated with the electrosurgical electrode while rotating the electrosurgical electrode; and
    adjusting the speed of rotation of the electrosurgical electrode based on the monitoring step to maintain an effective arc.

2. The method according to claim 1, wherein the monitoring step is carried out by monitoring a change in electrical impedance.

3. The method according to claim 1, wherein the monitoring step is carried out by monitoring a change in voltage.

4. The method according to claim 1, wherein the monitoring step is carried out by monitoring a change in current.

5. The method according to claim 1, wherein the monitoring step is carried out by monitoring electrical impedance.

6. The method according to claim 1, wherein the monitoring step is carried out by monitoring voltage.

7. The method according to claim 1, wherein the monitoring step is carried out by monitoring current.

8. The method according to claim 5, wherein the monitoring step is carried out by monitoring for an electrical impedance between about 700–1200 ohms.

9. The method according to claim 5, wherein the monitoring step is carried out by monitoring for an electrical impedance value below about 700 ohms.

10. The method according to claim 5, wherein the monitoring step is carried out by monitoring for an electrical impedance value below about 800 ohms.

11. The method according to claim 5, wherein the monitoring step is carried out by monitoring for an electrical impedance value above about 1200 ohms.

12. The method of claim 1, further comprising the step of providing feedback to a user based upon the monitoring step to adjust the speed of the electrosurgical electrode.

13. The method of claim 12, wherein the feedback to the user comprises audio feedback.

14. The method of claim 12, wherein the feedback to the user comprises visual feedback.

15. The method of claim 1, further comprising the step of adjusting the energy delivered to the electrosurgical electrode based upon the monitoring step so to at least help maintain an effective arc.

16. The method of claim 1, further comprising the step of monitoring the electrical characteristic to determine when an arc has been initiated based upon the monitoring step before moving the electrosurgical electrode.

17. The method according to claim 16, wherein the monitoring step is carried out by monitoring for an electrical impedance over 500 ohms.

18. The method according to claim 16, wherein the monitoring step is carried out by monitoring for an electrical impedance value over 2-times a baseline electrical impedance value.

19. The method according to claim 16, wherein the monitoring step is carried out by monitoring for an electrical impedance value over 2.5-times a baseline electrical impedance value.

20. A method for controlling the operation of a percutaneously-placed electrosurgical electrode of an electrosurgical device within a target tissue comprising:
    inserting the electrosurgical electrode into the target tissue;
    moving the electrode to a radially extended, outwardly bowed, operational state;
    delivering energy to a percutaneously-placed electrosurgical electrode to create an arc thereat while rotating said electrode to cut a target tissue;
    monitoring an electrical characteristic associated with the electrosurgical electrode while rotating the electrosurgical electrode; and
    adjusting the speed of rotation of the electrosurgical electrode based upon the monitoring step to maintain an effective arc.

* * * * *

UNITED STATES PATENT AND TRADEMARK OFFICE
CERTIFICATE OF CORRECTION

PATENT NO. : 7,189,232 B2
APPLICATION NO. : 11/433272
DATED : March 13, 2007
INVENTOR(S) : Scholl et al.

It is certified that error appears in the above-identified patent and that said Letters Patent is hereby corrected as shown below:

On the title page, item (73), delete "Ethicon Endo-Surgery, Inc., Cincinnati, OH" and insert -- Artemis Medical, Inc., Hayward, CA --

Signed and Sealed this

Ninth Day of October, 2007

JON W. DUDAS
*Director of the United States Patent and Trademark Office*